(12) United States Patent
Jones

(10) Patent No.: US 6,440,108 B1
(45) Date of Patent: Aug. 27, 2002

(54) SURGICAL NEEDLE HOLDER

(76) Inventor: Michael Harold Jones, 24H Old Bath Road, Cheltenham, Gloucestershire (GB)

( * ) Notice: Subject to any disclaimer, the term of this patent is extended or adjusted under 35 U.S.C. 154(b) by 0 days.

(21) Appl. No.: 09/600,492

(22) PCT Filed: Jan. 15, 1999

(86) PCT No.: PCT/GB99/00142

§ 371 (c)(1),
(2), (4) Date: Jul. 13, 2000

(87) PCT Pub. No.: WO99/35985

PCT Pub. Date: Jul. 22, 1999

(30) Foreign Application Priority Data

Jan. 16, 1998 (GB) .............................. 9800792

(51) Int. Cl.$^7$ ............................ A61M 25/00
(52) U.S. Cl. ............................ 604/264; 604/21; 606/44
(58) Field of Search ................ 604/264, 272, 604/21; 606/44

(56) References Cited

U.S. PATENT DOCUMENTS

| 3,799,168 | A |   | 3/1974  | Peters          |         |
|-----------|---|---|---------|-----------------|---------|
| 4,170,234 | A |   | 10/1979 | Graham          |         |
| 5,423,770 | A | * | 6/1995  | Yoon            | 604/506 |
| 5,599,348 | A | * | 2/1997  | Gentelia et al. | 604/21 X|
| 5,891,139 | A |   | 4/1999  | Cary, III       |         |
| 6,162,221 | A | * | 12/2000 | Ouchi           | 604/21 X|

FOREIGN PATENT DOCUMENTS

| DE | 295 03 626.5 |   | 4/1995 |        |
|----|--------------|---|--------|--------|
| EP | 0 069 207    |   | 1/1983 |        |
| EP | 0 371 829    |   | 6/1990 |        |
| GB | 2136296 A    | * | 9/1984 | 606/44 |

* cited by examiner

*Primary Examiner*—Gregory Huson
*Assistant Examiner*—Kathleen J. Prunner
(74) *Attorney, Agent, or Firm*—Baker Botts L.L.P.

(57) ABSTRACT

The surgical needle holder has a support body formed of an electrically conducting material and constituted by an outer cylindrical tube and an inner core. The outer cylindrical tube and the exposed parts of the core are surrounded by an insulating jacket. At one end of the core extends a blind bore or passageway into which the shank of the surgical needle is inserted. The blind bore or passageway crosses a cylindrical cavity formed in the core. The cavity has a vertical face and an opposing inclined face. The cavity is accessible through a slot formed in the surface of the outer cylindrical tube. A releasable locking device is formed by an electrically conducting plate having an insulated tab portion. The plate is mounted for pivotal movement from an upright position to a maximum forward inclined position and occupies the cavity with the insulated tab portion extending outwardly through the slot to the exterior of the support body. The plate also has a central aperture which, when in its upright pivotal position, is in alignment with the blind bore which has the same diameter. A coiled spring is housed in a groove formed in the inner core and surrounded by the outer cylindrical tube. The spring engages and urges the conducting plate to its maximum forward portion.

6 Claims, 1 Drawing Sheet

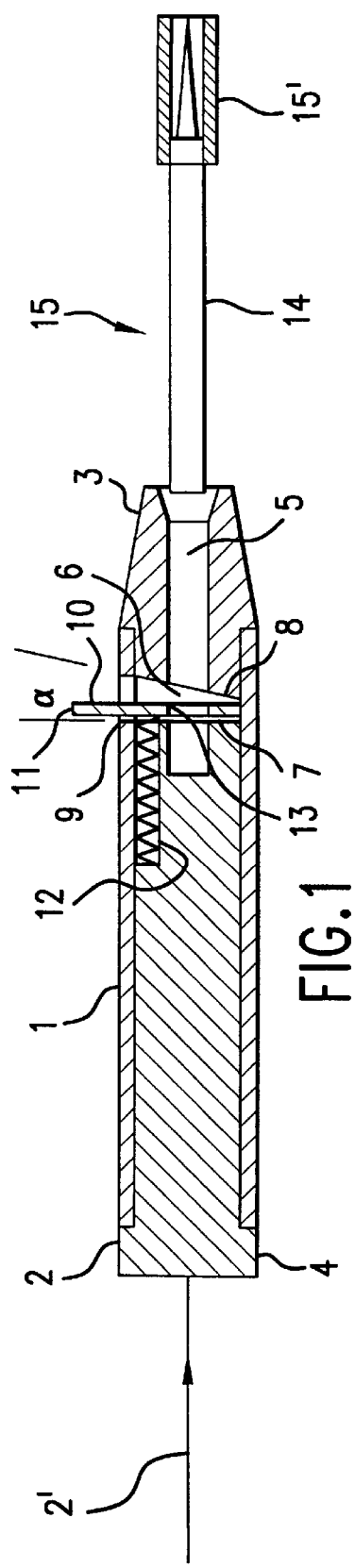
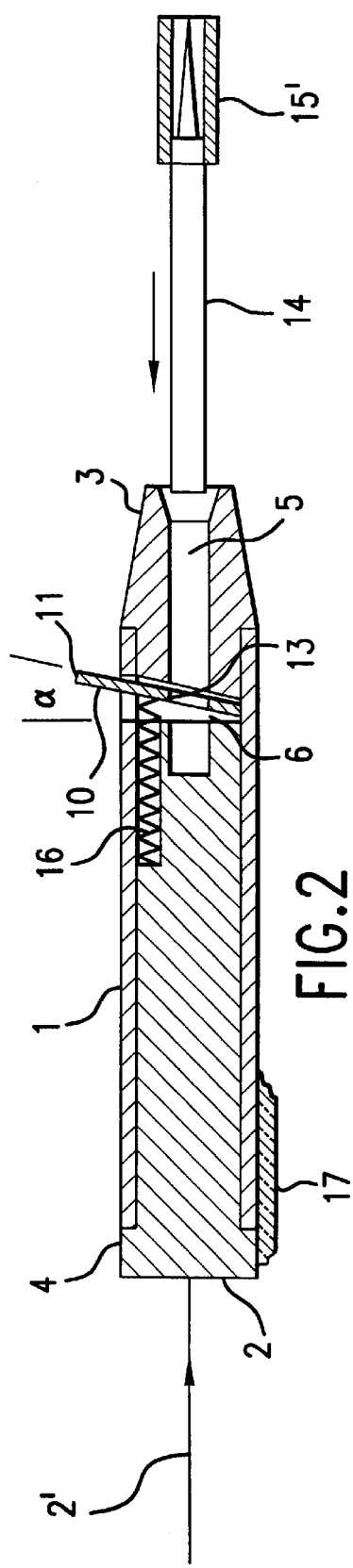
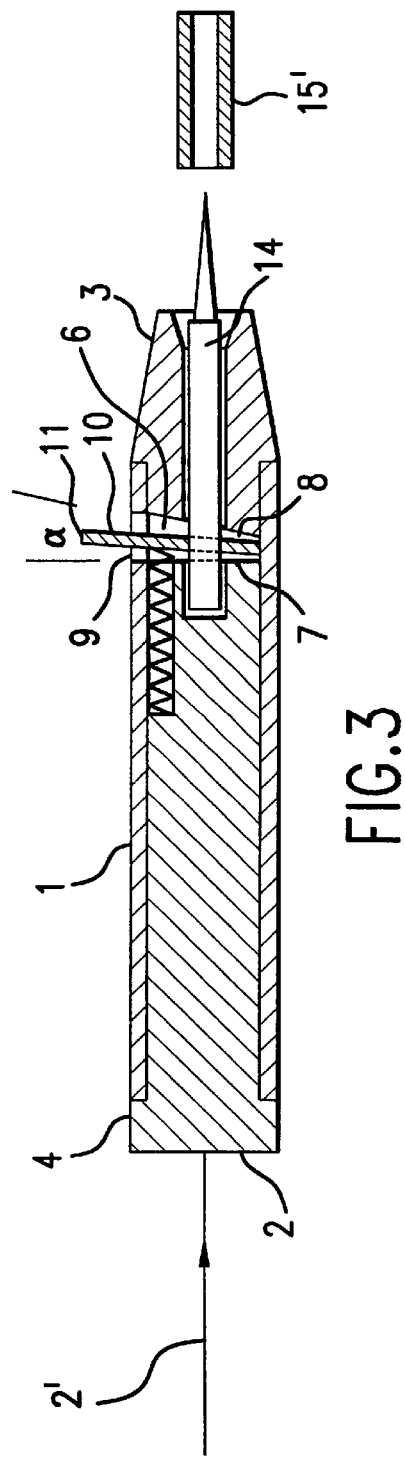

SURGICAL NEEDLE HOLDER

FIELD OF THE INVENTION

The present invention relates to a surgical needle holder and particularly to a surgical needle holder provided with a releasable locking mechanism for a surgical needle to be retained in the holder.

BACKGROUND OF THE INVENTION

Surgical needles mounted in specially designed holders are used in medical practice in the areas of for example hair removal by electrolysis such as during ophthalmic treatment, and certain aspects of cosmetic surgery.

Handling and disposal is important in the use of surgical needles both from the point of view of the health of the patient and the user.

There are various types of surgical needle holders in use at the present time. In one variant the surgical needle is held to the electrically conducting core of the needle holder by means of a mechanism operating in the manner of a drill chuck and in another in the manner of a propelling pencil.

The first arrangement, during mounting and disposal, necessitates far too much handling of the surgical needle to be acceptable while in the second arrangement the mechanism is not capable of holding the needle in the holder as firmly and positively to the extent required so that amongst other things electrical contact between the needle and the core of the holder is compromised.

SUMMARY OF THE INVENTION

It is an object of the present invention to overcome the disadvantages of the prior art.

According to the invention there is provided a surgical needle holder comprising an insulated electrically conducting support body for mounting a surgical needle, a passageway in the body for insertion of the needle shank, and releasable locking means in the passageway for locking the needle shank therein, and in electrical contact with the support body.

Preferably the locking means is in the form of a pivotal locking plate mounted in the support body and provided with an aperture for receiving the needle shank in one pivotal position of the locking plate when the shank is inserted in the passageway in the support body. The locking plate is biased to a normally held second pivotal position whereat the plate locks onto the needle shank around the plate aperture to secure the needle shank in the passageway.

Advantageously the locking plate is biased to the normally held second pivotal position by means of a coiled spring housed in the support body.

BRIEF DESCRIPTION OF THE DRAWINGS

Other features and advantages of the present invention will become apparent from the following description of a preferred embodiment thereof taken with reference to the accompanying drawings wherein:

FIG. 1 is a cross section of a surgical needle holder according to the invention showing the locking mechanism for the surgical needle in one operating position;

FIG. 2 is the same view as of a surgical holder according to the invention as FIG. 1 but with the locking mechanism in a different operating position: and FIG. 3 is the same cross sectional view of the surgical needle holder according to the invention as FIGS. 1 and 2 but showing a surgical needle locked in the holder by means of the locking mechanism.

BEST MODES OF CARRYING OUT THE INVENTION to The surgical holder shown in the drawings comprises an outer cylindrical tube 1, having an inner core 2 forming a projecting nozzle 3 at one end of the tube 1 and a butt end 4 at the rear of the tube 1. The tube 1 and core 2 form a support body formed of an electrically conducting material, and the core 2 is connectable to an R.F generator (not shown) through lead wire 2'.

The tube 1 and exposed parts of the core 2 are surrounded by an insulating jacket 17 (partially shown in FIG. 2).

A blind bore or passageway 5 extends into the core 2 of the surgical needle holder from the nozzle end 3. The blind bore 5 crosses a cylindrical cavity 6 formed in the core 2 having a vertical face 7 and an opposing face 8 inclined thereto at an angle α.

The cavity 6 is accessible through a slot 9 formed in the surface of the outer tube 1. An electrically conducting cylindrical plate 10 having an insulated tab portion 11 occupies the cavity with the tab portion 11 extending through the slot 9 in the outer tube 1. The plate 10 forms a releasable locking means.

By reason of the opposing vertical and inclined faces 7,8 of the cavity 6 the plate 10 is pivotally movable from an upright position as shown in FIG. 1 to a maximum forward inclined position as shown in FIG. 2 and intermediate positions as illustrated in FIG. 3.

The plate 10 is urged to its maximum forward position as shown in FIG. 2 by means of a coiled spring 16 housed in a groove 12 formed in the core 2 and surrounded by the outer tube 1. The plate 10 has a central aperture 13 which, when in its upright pivotal position, is in alignment with the blind bore 5 having the same diameter.

One method of loading the surgical needle holder as described with a surgical needle will now be described with reference to the drawings.

In FIG. 2 the locking plate 10, is shown biased to its normal forward rest position.

The shank 14 of a surgical needle 15 covered with a protective sheath 15' is inserted into the blind bore 5 in the nozzle 3 of the outer body 1 until it encounters the aperture 13 in the locking plate 10.

The shank 14 of the surgical needle 15 engages the periphery of the aperture 13 in the locking plate 10 thereby to push the locking plate 10 anti-clockwise until the shank 14 engages the base of the blind bore at which point the spring 16 urges the locking plate 10 clockwise until the needle shank 14 is held in tight frictional fit and consequently in good electrical contact, within the aperture 13 in the locking plate 10. Any pull on the needle 15 tending to remove it from the bore 5 merely serves to increase the grip of the plate 10 in the shank 14. The sheath 15' may then be removed safely.

To release the needle 15 the tab 11 is pulled anti-clockwise by the operator to the position shown in FIG. 1 at which point the needle 15 may be released from the surgical holder under its own weight into a disposable container.

What is claimed is:

1. A surgical needle holder comprising an insulated electrically conducting support body for mounting a surgical needle, a passageway in the body for insertion of the needle shank, and releasable locking means in the passageway for locking the needle shank therein, and in electrical contact with the support body.

2. A surgical needle holder as claimed in claim 1 wherein the locking means is in the form of a pivotal locking plate mounted in the support body and provided with an aperture for receiving the needle shank when the shank is inserted in the passageway in the support body with the locking plate in one pivotal position, said locking plate being biased to a normally held second pivotal position whereat the plate locks onto the needle shank around the plate aperture to secure the needle shank in the passageway.

3. A surgical needle as claimed in claim 2 wherein the locking plate is mounted in a cavity in the support body, one face of the cavity lying at an inclination to an opposed face of the cavity thereby to provide a degree of operating movement of the plate from an upright position in said first pivotal position to an inclined position in said second pivotal position to lock onto the needle shank.

4. A surgical needle holder as claimed in claim 3 wherein the locking plate is biased to the normally held second pivotal position by means of a coiled spring housed in the support body.

5. A surgical needle holder as claimed in claim 4 wherein the locking plate is provided with an operating tab extending from the cavity in the support body.

6. A surgical needle holder as claimed in claim 3 wherein the locking plate is provided with an operating tab extending from the cavity in the support body.

* * * * *